(12) United States Patent
Messier

(10) Patent No.: US 6,224,655 B1
(45) Date of Patent: May 1, 2001

(54) BIOSTATIC AIR FILTER

(76) Inventor: Pierre Messier, 98 Cochand Street, Ste-Marguerite-du-Lac-Masson, Quebec (CA), J0T 1L0

( * ) Notice: Subject to any disclaimer, the term of this patent is extended or adjusted under 35 U.S.C. 154(b) by 0 days.

(21) Appl. No.: 09/184,634

(22) Filed: Nov. 3, 1998

(51) Int. Cl.⁷ .............................. B01D 29/56; B01D 39/14
(52) U.S. Cl. ................... 96/226; 55/467; 55/485; 55/486; 55/497; 55/500; 55/527
(58) Field of Search .................... 96/223, 226, 227; 55/385.2, 467, 485, 486, 497, 500, 524, DIG. 5, DIG. 24, 527

(56) References Cited

U.S. PATENT DOCUMENTS

| | | | |
|---|---|---|---|
| 5,478,377 | * 12/1995 | Scavnicky et al. | 96/223 |
| 5,626,820 | 5/1997 | Kinkead et al. | |
| 5,639,452 | 6/1997 | Messier . | |
| 5,772,738 | 6/1998 | Muraoka . | |
| 5,792,513 | * 8/1998 | Koslow et al. | 427/195 |
| 5,820,644 | * 10/1998 | Mori et al. | 55/385.3 |
| 5,840,245 | * 11/1998 | Coombs et al. | 422/4 |
| 5,874,052 | * 2/1999 | Holland | 422/171 |
| 6,036,738 | * 3/2000 | Shanbrom | 55/524 |

FOREIGN PATENT DOCUMENTS

| | | |
|---|---|---|
| 36 18 499 | 3/1987 | (DE) . |
| 2532188 | 8/1982 | (FR) . |
| 2671008 | 7/1992 | (FR) . |

* cited by examiner

*Primary Examiner*—David A. Simmons
*Assistant Examiner*—Robert A. Hopkins
(74) *Attorney, Agent, or Firm*—Ronald S. Kosie; Robert Brouillette

(57) ABSTRACT

A microbiocidal air filter assembly, for filtering air, having
  a) a housing component defining an air path
  b) an air filter component
  b) an air inlet, and
  d) an air outlet,
wherein the air filter component comprises a first air filter element and a second filter element, wherein the air filter component is disposed so as to intersect the air path for air flow communication between the air inlet and the air outlet through each of the air filter elements, wherein one of the air filter elements is a microbiocidal air filter element and comprises a demand disinfectant resin, the demand disinfectant resin being an iodinated strong base anion exchange resin.

82 Claims, 5 Drawing Sheets

BIOSTATIC AIR FILTER

This invention relates to a biostatic air filter assembly and system for filtering air. For the purpose of illustration and discussion the filter assembly and system will be discussed in relation to ventilation systems for buildings; however, it is to be understood that they may be used in other contexts e.g. they may be exploited in relation to a respiratory mask or canister whether powered or not. Thus for example a microbial assembly as discussed herein may be installed in the air flow passage of a ventilating system intended for sterilization or disinfection of air, i.e. for devitalization of airborne microorganisms.

Bio-static air filters have been used in hospital ventilation system to inhibit secondary in-hospital infection problems caused by airborne microorganisms (hereinafter called simply called microorganisms) released from the filters. Air filtering assemblies or apparatus are known which may entrap microorganisms. Additionally, various materials such as fungicide, silver or UV-light catalyst have also been applied on filter elements to enhance the reduction of organisms in air leaving the filter element. While such materials are known to be effective, none of them can eradicate organisms completely. Micro-entities which escape from these known type of filter arrangements can be released back into the air and provoke or cause secondary airborne infection.

In the case of a known (e.g. non-woven fabric) filter elements placed inside of an air-duct, some portion of organisms will as mentioned above nevertheless penetrate to the other side and be released back into the air. It is because the flow speed of organisms is nearly equivalent to the airflow itself. The contact or exposure time of organisms to micro biocidal materials is not long enough to achieve complete removal or disinfection of air. Due to such short contact time of organisms to a microbiocidal material, such a conventional (known) filter can not fully intercept all organisms so as to prevent the escape of some organisms back into the environmental air.

This it is believed may be one of the causes of secondary in-hospital infection problems.

Accordingly, it would be advantageous to have a means (i.e. a biostatic air filter means) that may provide an alternative means for the removal of organisms from air, e.g. enhance the removal of organisms from air.

In accordance with the present invention there is provided a microbiocidal air filter assembly, for filtering air, having a) a housing component defining an air path b) an air filter component b) an air inlet, and d) an air outlet, wherein said air filter component comprises a first air filter element and a second air filter element, wherein said air filter component is disposed so as to intersect said air path for air flow communication between said air inlet and said air outlet through each of the air filter elements, wherein one of said air filter elements is a microbiocidal air filter element and comprises a demand disinfectant resin, said demand disinfectant resin being an iodinated strong base anion exchange resin.

The present invention in accordance with a further aspect provides in a system for disinfecting air containing airborne microorganisms, said system comprising a) means for providing an air path for the movement of air therethrough, and b) an air filter component wherein said air filter component comprises a first air filter element and a second air filter element, wherein said air filter component is disposed so as to intersect said air path for air flow communication between said air inlet and said air outlet through each of the air filter elements, wherein one of said air filter elements is a microbiocidal air filter element and comprises a demand disinfectant resin, said demand disinfectant resin being an iodinated strong base anion exchange resin.

The microbiocidal air filter element may for example comprise an air permeable non-woven fibrous carrier to which the iodinated strong base anion exchange resin is held as described herein. The non-woven carrier may have a pair of opposed broad faces spaced apart by a carrier matrix and the air filter component may be disposed so as to intersect the air path for air flow communication through each of the broad faces. The iodinated strong base anion exchange resin may be in the form of particles; the particles may be held to each of the above mentioned broad faces. Alternatively, the particles of iodinated strong base anion exchange resin may be dispersed in the carrier matrix of the air filter element. The microbiocidal air filter element may be spaced apart (e.g. by an air space) from the other filter element which may or may not be microbiocidal in character. The microbiocidal air filter element and/or the other air filter element may be of planar or pleated form. The microbiocidal air filter element and the other air filter element may be spaced apart from each other or they may abut as desired or necessary.

The air filter component of a microbial air filter assembly (or of a system for disinfecting air), in accordance with the present invention, may be configured so as to comprise a third air filter element in addition to the above mentioned first and second air filter elements; in this case one of the three air filter elements may be disposed between the other filter elements so as to define an intermediate filter element. The first air filter element may, for example, be a microbiocidal air filter element and it may be disposed between the other filter elements so as to define the intermediate filter element. Alternatively, the intermediate air filter element may be a particulate non-microbiocidal air filter element.

More particularly the present invention provides in a (bio-static or microbiocidal) air filter assembly for filtering air having a) a housing component defining an air path b) an air filter component b) an air inlet, and d) an air outlet, wherein said air filter component is disposed so as to intersect said air path for air flow communication between said air inlet and said air outlet through said air filter component, the improvement wherein said air filter component comprises an upstream filter element, a downstream filter element, and an intermediate air filter element disposed between said upstream and downstream air filter elements, wherein said air filter component is disposed so as to intersect said air path for air flow communication between said air inlet and said air outlet through each of the air filter elements, wherein said upstream and downstream air filter elements are each microbiocidal air filter elements and each comprises a demand disinfectant resin, said demand disinfectant resin being an iodinated strong base anion exchange resin.

The present invention further provides in a system for disinfecting air containing airborne microorganisms, said system comprising a) means for providing an air path for the movement of air therethrough, and b) an air filter component
wherein said air filter component is disposed so as to intersect said air path for air flow through said air filter component, the improvement wherein said air filter component comprises an upstream filter element, a downstream filter element and an intermediate air filter element disposed between said upstream and downstream air filter elements, wherein said air filter component is disposed so as to intersect said air path for air flow through each of the air filter elements, wherein said upstream and downstream air filter elements are each microbiocidal air filter elements and each comprises a demand disinfectant resin, said demand disinfectant resin being an iodinated strong base anion exchange resin; in accordance with the present invention said upstream and downstream air filter elements may each comprise an air permeable non-woven fibrous carrier to which said iodinated strong base anion exchange resin is held.

In accordance with the present invention a herein described air filter assembly may be disposed in the airflow passage of an air ventilating system.

The above mentioned assembly and system may be used in the context of air ventilation systems for buildings or if appropriately sized for gas masks or the like.

The upstream and downstream air filter elements may for example each comprise an air permeable non-woven fibrous carrier to which the iodinated strong base anion exchange resin may be held. The iodinated strong base anion exchange resin may be in the form of particles.

In accordance with t he present invention, the iodinated resin may be an iodinated resin as described in U.S. Pat. No. 5,639,452; such (particulate) iodinated resin may be obtained under the Triosyn brand name from Hydro-Biotech Inc., St Jerome, Quebec, Canada. The non-woven fibrous carrier may be of any suitable (known) material keeping in mind the purpose of the air filter; the non woven carrier may, for example, be a non-woven fabric, a non-woven fibrous carrier such as, for example, described in U.S. Pat. No. 5,626,820 or the like.

The iodinated strong base anion exchange resin may for example, be in the form of particles; it may take other forms keeping in mind the purpose of an air filter element, i.e. to be permeable to air. The non-woven carrier of each of the upstream and downstream filter elements may have a pair of opposed broad faces spaced apart by a carrier matrix; in this case the air filter component may be disposed so as to intersect the air path for air flow communication through each of the broad faces; see U.S. Pat. No. 5,626,820.

In accordance with the present invention particles of the iodinated strong base anion exchange resin may be held (e.g. by an adhesive) to one or each of said broad faces, e.g. the faces may have a coating like resin particle layer. In accordance with the present invention particles of said iodinated strong base anion exchange resin may be dispersed in the carrier matrix of one or each of said upstream and downstream filter elements, e.g. particles may be bound in the interstices of the carrier matrix in any (known) manner sufficient to maintain them in place with the passage of air through the air permeable matrix. The particles of resin may, for example, be held to a carrier in a manner analogous to manners described in for particles in U.S. Pat. Nos. 5,639,452 and 5,626,820, the entire contents of both of which are incorporated herein by reference.

The intermediate, upstream and/or downstream air filter elements, may be of planar form or of pleated form.

In accordance with the present invention one or each of the upstream and downstream air filter elements may be spaced apart (e.g. by an air space) from the intermediate filter element; alternatively or additionally as the case may be one or each of the upstream and downstream air filter elements may abut the intermediate filter element.

The other intermediate air filter element, may be of any known kind; it may be a particulate filter; it may or may not have biocidal properties; etc. The other intermediate air filter element may likewise comprise a similar non-woven fibrous carrier. The other filter element may, for example, be a high efficiency particulate air filter (i.e. an HEPA filter). If such other intermediate air filter element has microbiocidal properties it may, for example, be A HEPA filter impregnated with fungicide agent;

A filter impregnated with silver based biostatic resin;

A HEPA filter impregnated with silver based biostatic resin;

A HEPA filter impregnated with light-activating catalyst; or

A HEPA filter impregnated with silver and manganese based bio-static material;

the other intermediate air filter element may, if desired, or necessary comprise an iodinated resin as described herein.

As mentioned above, the non-woven fibrous carrier of the upstream and/or downstream air filter elements may have iodinated resin dispersed therein, be coated with iodinated resin, or both (hereinafter sometimes referred to as the iodine membrane). If both upstream and downstream air filter elements are present they may be spaced apart from or be attached to a respective side of an intermediate mediocre quality air filter (hereinafter called mother filter). The mother filter and iodine membranes may as desired or necessary both have a pleated (i.e. zigzag) form; the mother filter and iodine membranes may as desired or necessary both have a planar (i.e. relatively flat) form; or one of the mother filter and iodine membranes may as desired or necessary have a pleated (i.e. zigzag) form and the other(s) a planar form. The filter assembly may thus comprise a multi-layer of non-woven fibrous material.

Advantageously, the intermediate air filter layer is of pleated (zigzag) form. Since iodine membranes are attached on both front and rear of a zigzag folded mother filter, the reduction ratio of organisms (e.g. percentage of microorganisms devitalised) may be enhanced over the mother filter alone. As the exposure (i.e. residence) time is increased, entrapped organisms are more likely to be brought into contact with iodinated resin and be destroyed. Also, the increased surface area of zigzag folded mother filter unit will further enhance organism reduction efficiency. The structure of the filter assembly or unit is relatively simplified if the mother filter is zigzag folded whereas the cross section of iodine membranes are flat or wave shaped.

As mentioned above, a sterilizing filter assembly of the present invention may be placed or installed in the air flow passage of a ventilating system for the filtration of air to be passed therethrough.

In the drawings which illustrate example embodiments of the present invention:

Figure 1:
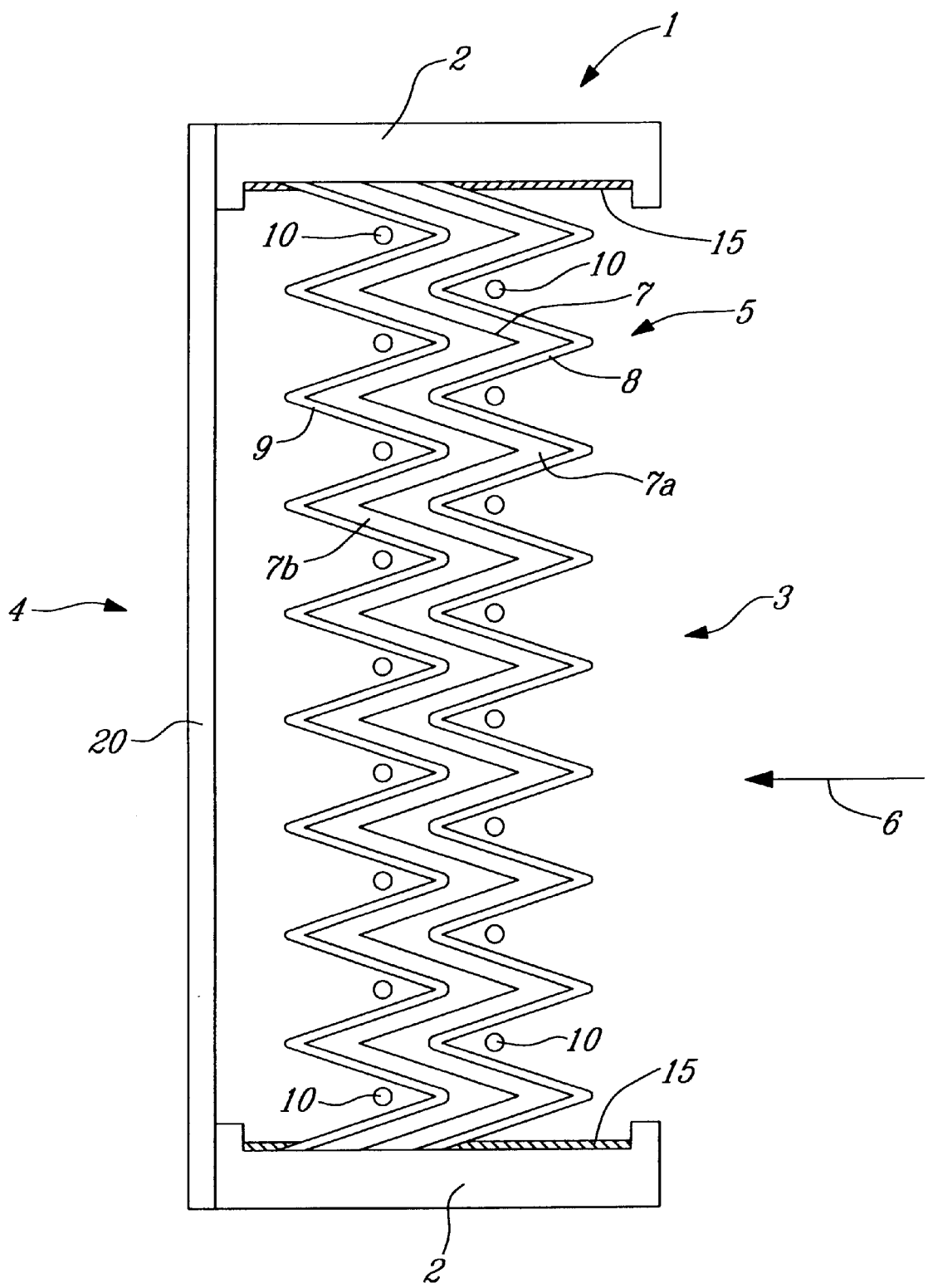
FIG. 1 is a schematic cross-sectional side view of an example embodiment of an air filter assembly in accordance with the present invention.
Figure 2:
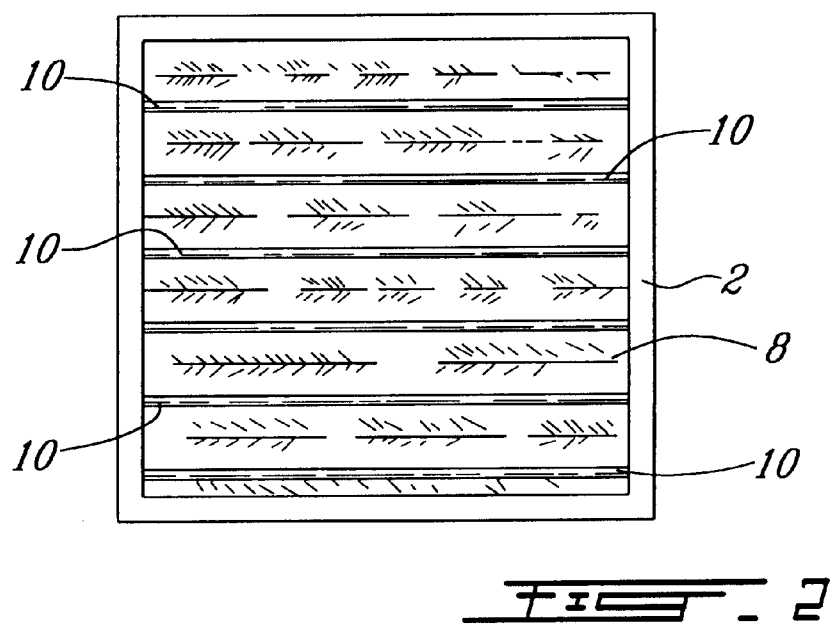
FIG. 2 is a face on view of the assembly of FIG. 1 in the direction of the arrow showing a broad face of the filter component through which air to be filtered is to pass.
Figure 3:
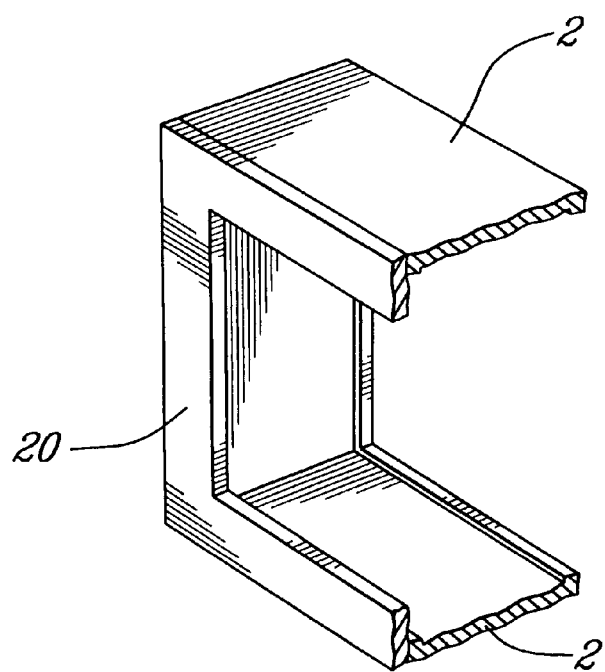
FIG. 3 is a schematic perspective cross-sectional view of the housing component of the assembly of FIG. 1 without the air filter component disposed therein across the air path defined thereby.

Referring to FIGS. 1, 2 and 3 these figures illustrate an air filter assembly 1 in accordance with the present invention which has a housing member 2 having an upstream side and a downstream side designated generally by the reference numerals 3 and 4 respectively. A three part air filter component 5 is disposed in the housing member 2 such that it intersects the air path between the upstream and downstream sides 3 and 4 of the housing member 2, i.e. air flowing through the housing member 2, in the direction of the arrow 6, from the upstream side 3 to the downstream side 4, flows through each of the elements of the air filter component 5. The air filter component 5 comprises a mother or intermediate filter 7 and opposed upstream and downstream air filter elements (i.e. iodine membranes) designated generally by the reference numerals 8 and 9 respectively. The intermediate air filter element 7 has a pleated or zigzag form (i.e. in cross-section). Both of the iodine membranes 8 and 9 on either side of the intermediate filter element 7 also have a pleated form and are spaced apart from the intermediate filter element 7 so as to define thereby a pair of zigzag air spaces 7a and 7b. Thus as may be seen the air filter component as a whole has a pleat like form; the increased surface area of the zigzag folded filter component may provide for an enhanced reduction of viable microbes. Support bars 10 are disposed in the exposed valleys of the zigzag folds of the air filter component 5 for maintaining the form of the air filter component 5 during use; the opposed ends of each of the bars 10 are attached in any suitable manner to the housing member, e.g. adhesive, welding, etc,.

The upstream and downstream air filter elements 8 and 9 (i.e. iodine membranes), instead of being spaced apart from the intermediate air filter element 7, if desired, may, for example, be attached to or abut the intermediate air filter element 7. The upstream and downstream air filter elements 8 and 9 may be attached to the intermediate air filter element 7 by a suitable adhesive or the like; such adhesive is of course to be applied keeping in mind the air permeability of the air filter component.

Any gaps between housing member 2 and the air filter component 5 may be filled with (suitable) adhesive or caulking 15 to achieve airtight engagement between the periphery of the air filter component and the inner wall surface of the housing member 2, i.e. the air filter component 5 may be attached to the housing member 2 by the adhesive 15. A peripheral frame-like reinforcement member 20 may be attached to one side of housing member 2 in order to provide reinforcement of the air filter assembly 1 in a ventilation duct, i.e. to firmly sustain the unit inside a ventilation duct. The periphery of the frame-like member 20 may also, if desired or necessary, be provided with a gasket or packing member to provide air-tight engagement between the housing member 2 and the inner wall surface of the duct of an air ventilation system.

The intermediate air filter element 7 may be glass wool or fiberglass layered with synthetic fibers configured so as to be able to capture particulate matter such as microorganisms. The iodine membranes (i.e. upstream and downstream air filter elements 8 and 9 respectively) have a structure as described above. Thus, as air passes through the air filter component 5 microorganisms may be entrapped (e.g. in the zigzag air spaces and by the intermediate filter element) and be devitalized (i.e. rendered harmless) by the upstream and downstream air filter elements 8 and 9 upon contact with the demand iodinated resin thereof. Since upstream and downstream air filter elements 8 and 9 are disposed on both sides of the intermediate filter, organisms entrapped in the zigzag air spaces 7a and 7b will be exposed to the possibility of contact with the demand iodinated resin of the upstream and downstream air filter elements for an increased period of time so as to provide enhanced eradication thereof. An air filter component 5 as shown in FIG. 1 (as well as those shown in FIGS. 4 and 5 described below) thus provide a means for the attenuation of secondary in hospital infections caused by the release of viable microorganisms back into hospital air.

Figure 4:
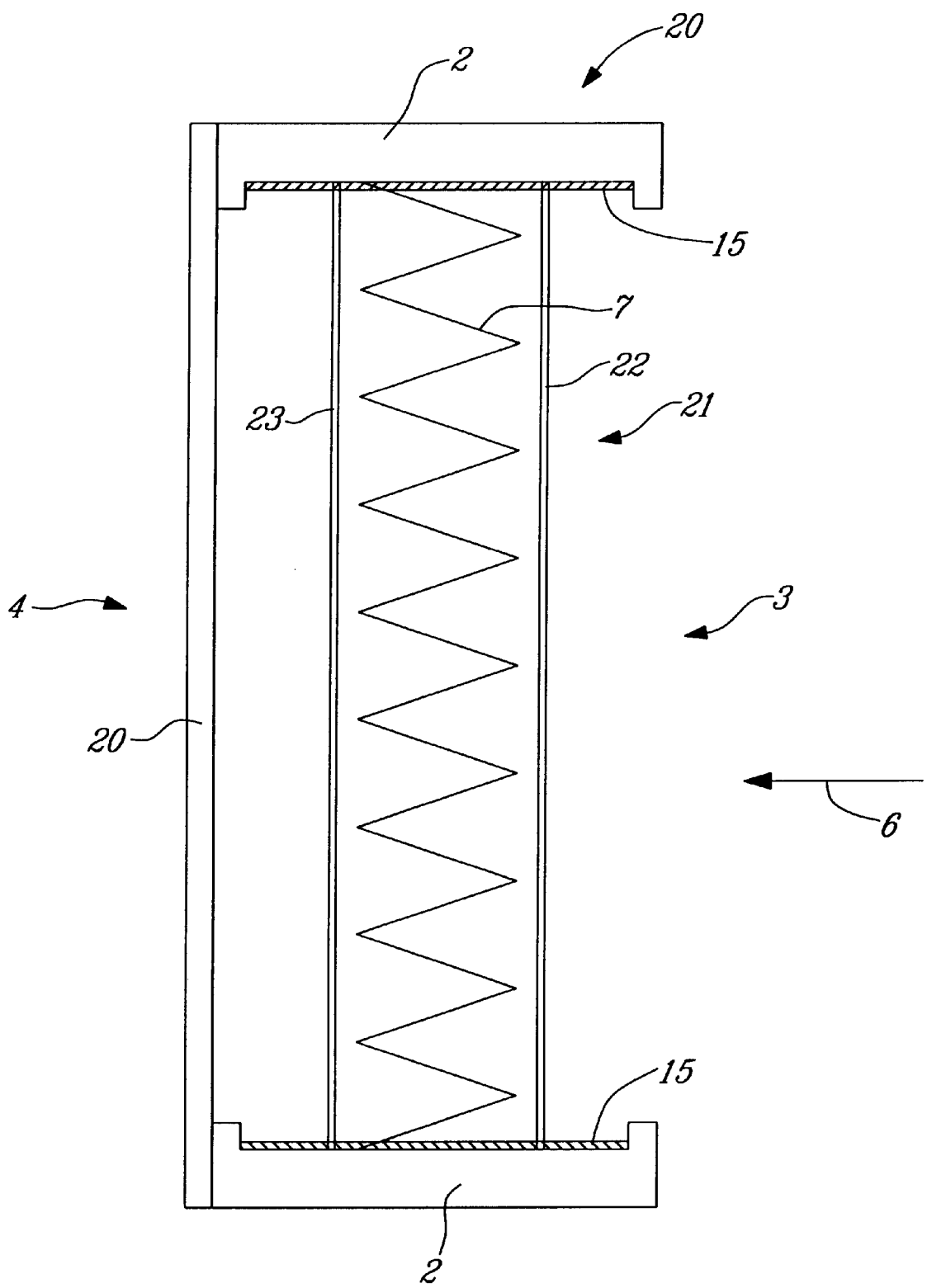
FIG. 4 is a schematic cross-sectional side view of another example embodiment of an air filter assembly in accordance with the present invention.

FIG. 4 illustrates an additional embodiment of an air filter assembly 20 in accordance with the present invention. The embodiment illustrated in this figure is the same as shown in FIG. 1 except for the air filter component 21; accordingly, the same reference numerals are used for common elements. The air filter component 20 of FIG. 4, has flat or planar shaped (i.e. in cross-section) upstream and downstream air filter elements 22 and 23 respectively which are each spaced apart from a respective side face of the pleated or zigzag folded intermediate filter element 7. Under such an arrangement, organisms may be entrapped between the intermediate air filter element 7 and the upstream and downstream air filter elements 22 and 23 and be devitalized upon contact with the demand iodinated resin of upstream and downstream air filter elements 22 and 23. This configuration thus will lead to similar results like filter assembly 1, but the structure will be such simpler due to the flat shape of the upstream and downstream air filter elements 22 and 23 and absence of support bars 10.

Figure 5:
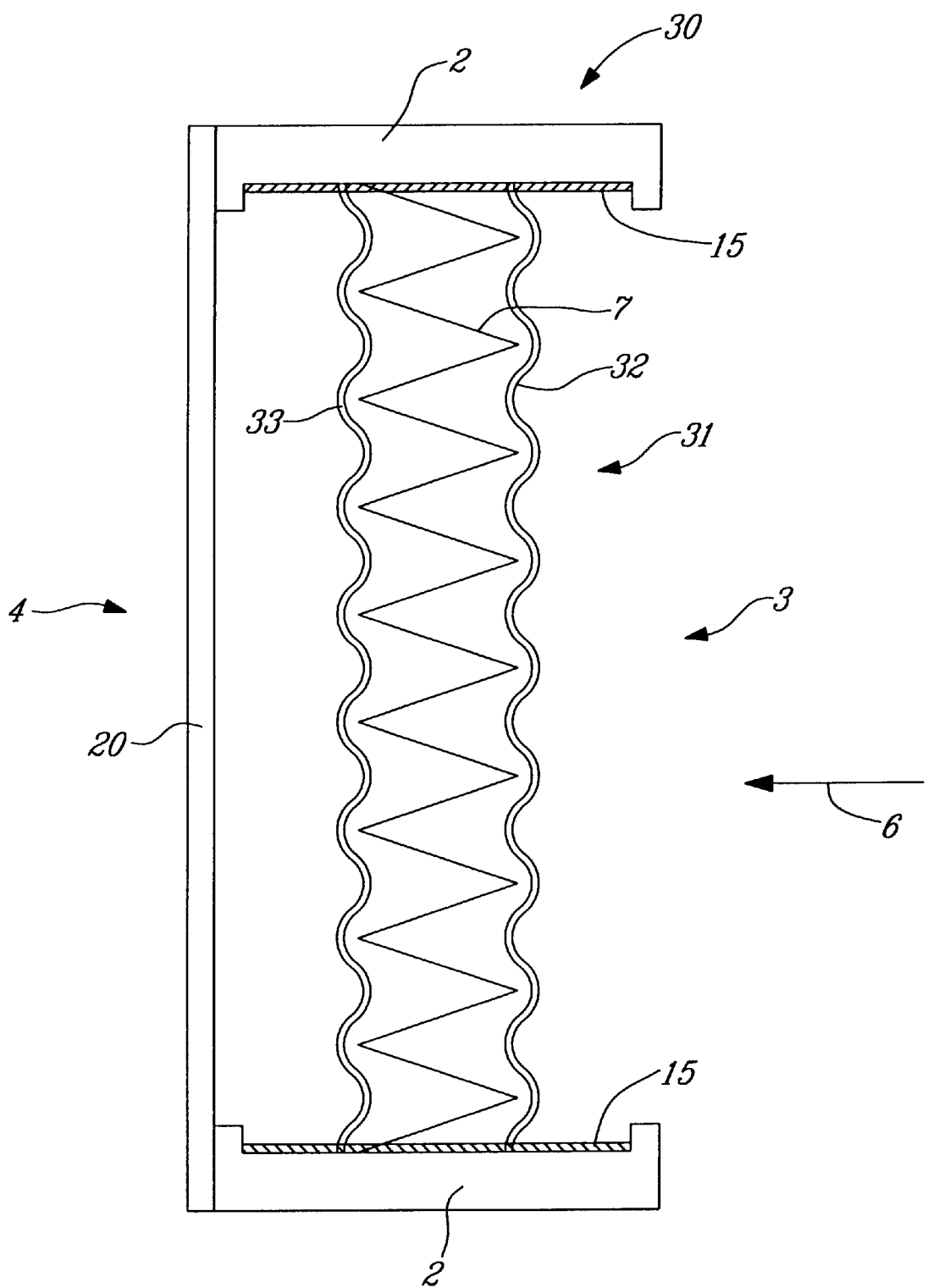
FIG. 5 is a schematic cross-sectional side view of a further example embodiment of an air filter assembly in accordance with the present invention.

FIG. 5 illustrates another embodiment of an air filter assembly 30 in accordance with the present invention. The embodiment illustrated in this figure is the same as shown in FIG. 1 except for the air filter component 31; accordingly, the same reference numerals are used for common elements. The air filter component 31 of FIG. 5, has undulating or wave shaped (i.e. in cross-section) upstream and downstream air filter elements 32 and 33 respectively which are each spaced apart from a respective side face of the pleated or zigzag folded intermediate filter element 7. This configuration will give similar result as above, but has an advantage of increased surface area as well as ease of manufacturing.

Figure 6:
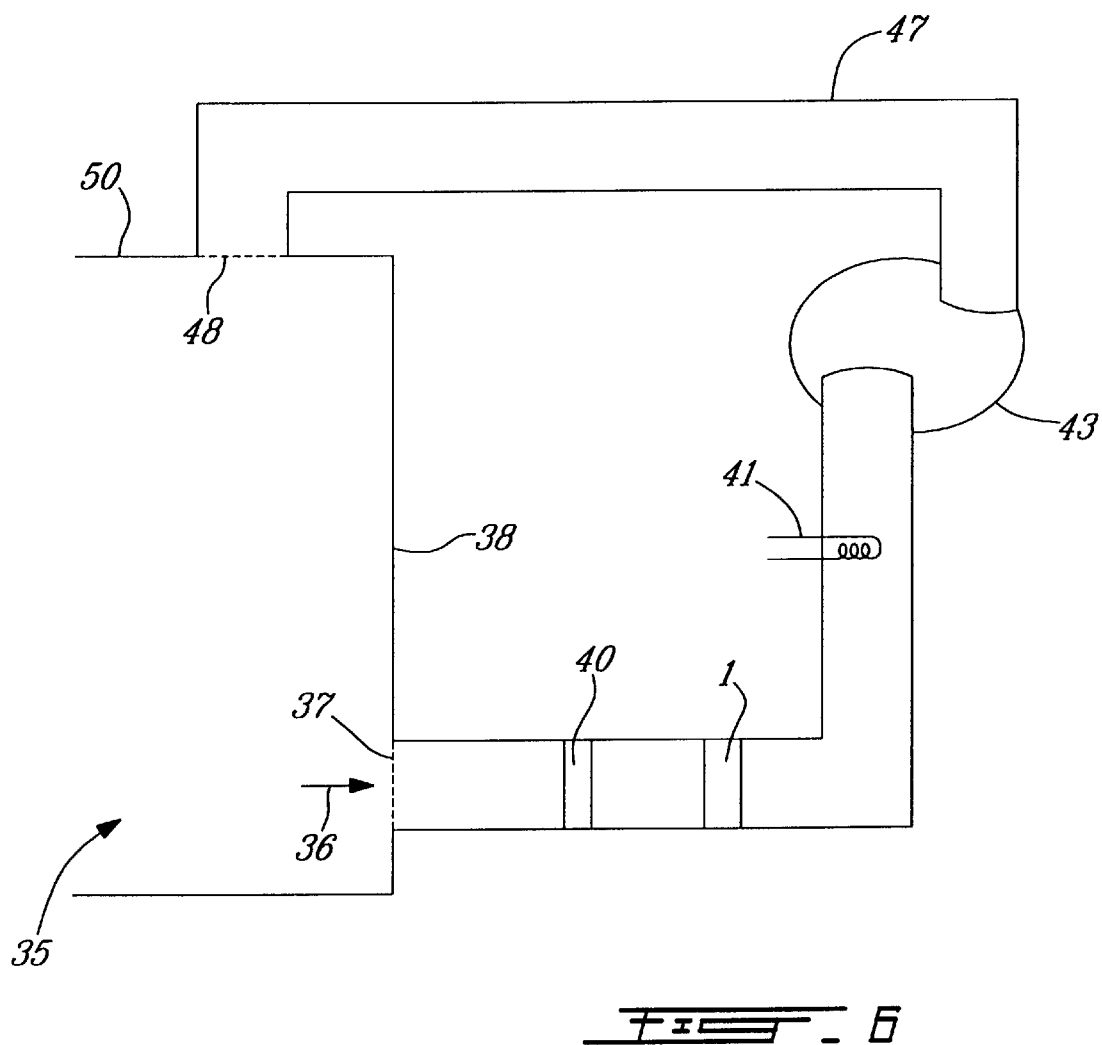
FIG. 6 is schematic illustration of the filter assembly of FIG. 1 installed in the air passage of ventilator system.

FIG. 6 illustrates the air filter assembly 1 of FIG. 1 installed in the air passage of a ventilator system for a room 35. Input (or contaminated) air 36 flows into the ventilator system through air entrance opening 37 on the wall 38, and thereafter, in sequence, through a dust removal pre-filter 40, air filter assembly 1 as shown in FIG. 1 (i.e. through the three air filter elements) and cool/hot water coil 41 (for temperature adjustment if necessary or desired), into air-circulating fan 43. The outlet of fan 43 is connected to air duct 47 which provides an air path for cleaned air flow back into the room 35 through air exhaust outlet 48 located on the ceiling 50 of room 35. The biocidal performance of the system may be stronger during the night when the system it is not usually running. Therefore, if the system is operated during daytime and is stopped overnight, the removal efficiency of micro-entities may be enhanced.

Although the air filter component is shown in FIGS. 1 to 5 as having two (2) iodine membranes the air filter component may have only one of such iodine membranes, e.g. the air filter component is shown in FIG. 1 may have only an upstream air filter element 8 or a downstream air filter element 9.

Comparison tests of an air filter assembly in accordance with the present invention were conducted against other biostatic filters(no iodine), described below:

Test Sample 1:
HEPA filter impregnated with fungicide agent.

Test Sample 2:
Mediocre performance filter impregnated with silver based biostatic resin (Brand name: Ameni-top)

Test Sample 3:
HEPA filter impregnated with silver based biostatic resin (Brand name: Ameni-top).

Test Sample 4:
HEPA filter impregnated with light-activating catalyst

Test Sample 5:
HEPA filter impregnated with silver and manganese based bio-static material The test result are outlined in table 1 below which shows percentage removal of microorganisms from air over time:

| Elapsed time (Hours) | Invented Filter assembly | Test Sample 1 | Test Sample 2 | Test Sample 3 | Test Sample 4 | Test Sample 5 |
|---|---|---|---|---|---|---|
| 0 | 100% | 73.00% | 97.40% | 83.00% | 98.80% | 10.60% |
| 1 | 100% | 86.00% | 99.70% | 84.00% | 97.50% | 35.00% |
| 2 | 100% | 76.00% | 99.50% | 90.10% | 95.90% | 43.10% |
| 4 | 100% | 80.00% | 99.60% | 90.00% | 99.10% | 34.50% |
| 6 | 100% | 79.00% | 99.60% | 88.00% | 98.80% | 95.10% |
| 24 | 100% | 85.00% | 99.70% | 92.80% | 97.20% | 88.6 |

As may be seen from table 1, the air filter assembly of the present invention has an enhanced microbial removal ratio as compared to the other test samples. Accordingly, a air filter assembly in accordance with the present invention may thus attenuate or even eliminate secondary in hospital infection problems caused by the re-release of once-entrapped organisms.

I claim:

1. In a microbiocidal air filter assembly, for filtering air, having
    a) a housing component defining an air path
    b) an air filter component
    b) an air inlet, and
    d) an air outlet,
        wherein said air filter component comprises a microbiocidal air filter element, wherein said air filter component is disposed so as to intersect said air path for air flow communication between said air inlet and said air outlet through said microbiocidal air filter element, the improvement wherein said air filter component comprises an upstream filter element and a downstream filter element, said microbiocidal air filter element being disposed between said upstream and downstream filter elements so as to define an intermediate air filter element, wherein said air filter component is disposed so as to intersect said air path for air flow communication between said air inlet and said air outlet through each of the air filter elements, wherein said upstream and downstream air filter elements are each microbiocidal air filter elements, wherein said upstream and downstream air filter elements each comprises a demand disinfectant resin, said demand disinfectant resin being in the form of particles of an iodinated strong base anion exchange resin and wherein each of said upstream and downstream air filter elements is spaced apart by an air space, from said intermediate filter element.

2. A microbiocidal air filter assembly as defined in claim 1 wherein said upstream and downstream air filter elements each comprise an air permeable non-woven fibrous carrier to which said iodinated strong base anion exchange resin is held.

3. A microbiocidal air filter assembly as defined in claim 2 wherein said iodinated strong base anion exchange resin is in the form of particles, wherein the non-woven carrier of each of said upstream and downstream filter elements has a pair of opposed broad faces spaced apart by a carrier matrix and wherein said air filter component is disposed so as to intersect said air path for air flow communication through each of said broad faces.

4. A microbiocidal air filter assembly as defined in claim 3 wherein particles of said iodinated strong base anion exchange resin are held to each of said broad faces.

5. A microbiocidal air filter assembly as defined in claim 3 wherein particles of said iodinated strong base anion exchange resin are dispersed in the carrier matrix of each of said upstream and downsteam filter elements.

6. A microbiocidal air filter assembly as defined in claim 1 wherein said intermediate air filter element is of planar form.

7. A microbiocidal air filter assembly as defined in claim 1 wherein said intermediate air filter element is of pleated form.

8. A microbiocidal air filter assembly as defined in claim 7 wherein said upstream and downstream air filter elements are each of pleated form.

9. In a system for disinfecting air containing airborne microorganisms, said system comprising
    a) means for providing an air path for the movement of air therethrough, and
    b) an air filter component
        wherein said air filter component comprises a microbiocidal air filter element, wherein said air filter component is disposed so as to intersect said air path for air flow through said microbiocidal air filter element,
        the improvement wherein said air filter component comprises an upstream filter element and a downstream filter element, said microbiocidal air filter element being disposed between said upstream and downstream filter elements so as to define an intermediate air filter element, wherein said air filter component is disposed so as to intersect said air path for air flow through each of the air filter elements, wherein said upstream and downstream air filter elements are each microbiocidal air filter elements, wherein said upstream and downstream air filter elements each comprises a demand disinfectant resin, said demand disinfectant resin being in the form of particles an iodinated strong base anion exchange resin and wherein each of said upstream and downstream air filter elements is spaced apart, by an air space, from said intermediate filter element.

10. In a system for disinfecting air as defined in claim 9 wherein said upstream and downstream air filter elements each comprise an air permeable non-woven fibrous carrier to which said iodinated strong base anion exchange resin is held.

11. In a system for disinfecting air as defined in claim 10 wherein said iodinated strong base anion exchange resin is in the form of particles, wherein the non-woven carrier of each of said upstream and downstream filter elements has a pair of opposed broad faces spaced apart by a carrier matrix and wherein said air filter component is disposed so as to intersect said air path for air flow communication through each of said broad faces.

12. In a system for disinfecting air as defined in claim 11 wherein particles of said iodinated strong base anion exchange resin are held to each of said broad faces.

13. In a system for disinfecting air as defined in claim 11 wherein particles of said iodinated strong base anion exchange resin are dispersed in the carrier matrix of each of said upstream and downstream filter elements.

14. In a system for disinfecting air as defined in claim 9 wherein said intermediate air filter element is of planar form.

15. In a system for disinfecting air as defined in claim 9 wherein said intermediate air filter element is of pleated form.

16. In a system for disinfecting air as defined in claim 15 wherein said upstream and downstream air filter elements are each of pleated form.

17. In a microbiocidal air filter assembly, for filtering air, having
   a) a housing component defining an air path
   b) an air filter component
   b) an air inlet, and
   d) an air outlet,
      wherein said air filter component is disposed so as to intersect said air path for air flow communication between said air inlet and said air outlet through said air filter component,
      the improvement wherein said air filter component comprises an upstream filter element, a downstream filter element, and an intermediate air filter element disposed between said upstream and downstream air filter elements, wherein said air filter component is disposed so as to intersect said air path for air flow communication between said air inlet and said air outlet through each of the air filter elements, wherein said upstream and downstream air filter elements are each microbiocidal air filter elements, wherein said upstream and downstream air filter elements each comprises a demand disinfectant resin, said demand disinfectant resin being in the form of particles an iodinated strong base anion exchange resin and wherein each of said upstream and downstream air filter elements is spaced apart, by an air space, from said intermediate filter element.

18. In a system for disinfecting air containing airborne microorganisms, said system comprising
   a) means for providing an air path for the movement of air therethrough, and
   b) an air filter component
      wherein said air filter component is disposed so as to intersect said air path for air flow through said air filter component, the improvement wherein said air filter component comprises an upstream filter element, a downstream filter element and an intermediate air filter element disposed between said upstream and downstream air filter elements, wherein said air filter component is disposed so as to intersect said air path for air flow through each of the air filter elements, wherein said upstream and downstream air filter elements are each microbiocidal air filter elements, wherein said upstream and downstream air filter elements each comprises a demand disinfectant resin, said demand disinfectant resin being in the form of particles an iodinated strong base anion exchange resin, wherein each of said upstream and downstream air filter elements is spaced apart, by an air space, from said intermediate filter element and
      wherein said up stream and downstream air filter elements each comprise an air permeable non-woven fibrous carrier to which said iodinated strong base anion exchange resin is held.

19. A microbiocidal air filter assembly, for filtering air, having
   a) a housing component defining an air path
   b) an air filter component
   b) an air inlet, and
   d) an air outlet,
      wherein said air filter component comprises a first air filter element and a second air filter element, wherein said air filter component is disposed so as to intersect said air path for air flow communication between said air inlet and said air outlet through each of the air filter elements, wherein one of said air filter elements is a microbiocidal air filter element and comprises a demand disinfectant resin, said demand disinfectant resin being in the form of particles of an iodinated strong base anion exchange resin and wherein said first air filter element is spaced apart, by an air space, from said second air filter element.

20. In a system for disinfecting air containing airborne microorganisms, said system comprising
   a) means for providing an air path for the movement of air therethrough, and
   b) an air filter component
      wherein said air filter component comprises a first air filter element and a second air filter element, wherein said air filter component is disposed so as to intersect said air path for air flow communication between said air inlet and said air outlet through each of the air filter elements, wherein one of said air filter elements is a microbiocidal air filter element and comprises a demand disinfectant resin, said demand disinfectant resin being in the form of particles an iodinated strong base anion exchange resin and wherein said first air filter element is spaced apart, by an air space, from said second air filter element.

21. In a microbiocidal air filter assembly, for filtering air, having
   a) a housing component defining an air path
   b) an air filter component
   b) an air inlet, and
   d) an air outlet,
wherein said air filter component comprises a microbiocidal air filter element, wherein said air filter component is disposed so as to intersect said air path for air flow communication between said air inlet and said air outlet through said microbiocidal air filter element, the improvement wherein said air filter component consists of said microbiocidal air filter element, an upstream filter element and a downstream filter element, said microbiocidal air filter element being disposed between said upstream and downstream filter elements so as to define an intermediate air filter element, wherein said air filter component is disposed so as to intersect said air path for air flow communication between said air inlet and said air outlet through each of the air filter elements, wherein said upstream and downstream air filter elements are each microbiocidal air filter elements, wherein said upstream and downstream air filter elements each comprises a demand disinfectant resin, said demand disinfectant resin being in the form of particles of an iodinated strong base anion exchange resin, and wherein each of said upstream and downstream air filter elements is spaced apart, by an air space, from said intermediate filter element.

22. A microbiocidal air filter assembly as defined in claim 21 wherein said upstream and downstream air filter elements each comprise an air permeable non-woven fibrous carrier to which said iodinated strong base anion exchange resin is held.

23. A microbiocidal air filter assembly as defined in claim 22 wherein the non-woven carrier of each of said upstream and downstream filter elements has a pair of opposed broad faces spaced apart by a carrier matrix and wherein said air filter component is disposed so as to intersect said air path for air flow communication through each of said broad faces.

24. A microbiocidal air filter assembly as defined in claim 23 wherein particles of said iodinated strong base anion exchange resin are held to each of said broad faces.

25. A microbiocidal air filter assembly as defined in claim 23 wherein particles of said iodinated strong base anion exchange resin are dispersed in the carrier matrix of each of said upstream and downsteam filter elements.

26. A microbiocidal air filter assembly as defined in claim 21 wherein said intermediate air filter element is of planar form.

27. A microbiocidal air filter assembly as defined in claim 21 wherein said intermediate air filter element is of pleated form.

28. A microbiocidal air filter assembly as defined in claim 27 wherein said upstream and downstream air filter elements are each of pleated form.

29. In a system for disinfecting air containing airborne microorganisms, said system comprising
   a) means for providing an air path for the movement of air therethrough, and
   b) an air filter component
      wherein said air filter component comprises a microbiocidal air filter element, wherein said air filter component is disposed so as to intersect said air path for air flow through said microbiocidal air filter element,
      the improvement wherein said air filter component consists of said microbiocidal air filter element, an upstream filter element and a downstream filter element, said microbiocidal air filter element being disposed between said upstream and downstream filter elements so as to define an intermediate air filter element, wherein said air filter component is disposed so as to intersect said air path for air flow through each of the air filter elements, wherein said upstream and downstream air filter elements are each microbiocidal air filter elements, wherein said upstream and downstream air filter elements each comprises a demand disinfectant resin, said demand disinfectant resin being in the form of particles of an iodinated strong base anion exchange resin and wherein each of said upstream and downstream air filter elements is spaced apart, by an air space, from said intermediate filter element.

30. In a system for disinfecting air as defined in claim 29 wherein said upstream and downstream air filter elements each comprise an air permeable non-woven fibrous carrier to which said iodinated strong base anion exchange resin is held.

31. In a system for disinfecting air as defined in claim 30 wherein the non-woven carrier of each of said upstream and downstream filter elements has a pair of opposed broad faces spaced apart by a carrier matrix and wherein said air filter component is disposed so as to intersect said air path for air flow communication through each of said broad faces.

32. In a system for disinfecting air as defined in claim 31 wherein particles of said iodinated strong base anion exchange resin are held to each of said broad faces.

33. In a system for disinfecting air as defined in claim 31 wherein particles of said iodinated strong base anion exchange resin are dispersed in the carrier matrix of each of said upstream and downstream filter elements.

34. In a system for disinfecting air as defined in claim 29 wherein said intermediate air filter element is of planar form.

35. In a system for disinfecting air as defined in claim 29 wherein said intermediate air filter element is of pleated form.

36. In a system for disinfecting air as defined in claim 35 wherein said upstream and downstream air filter elements are each of pleated form.

37. In a microbiocidal air filter assembly, for filtering air, having
   a) a housing component defining an air path
   b) an air filter component
   b) an air inlet, and
   d) an air outlet,
      wherein said air filter component is disposed so as to intersect said air path for air flow communication between said air inlet and said air outlet through said air filter component,
      the improvement wherein said air filter component consists of an upstream filter element, a downstream filter element, and an intermediate air filter element disposed between said upstream and downstream air filter elements, wherein said air filter component is disposed so as to intersect said air path for air flow communication between said air inlet and said air outlet through each of the air filter elements, wherein said upstream and downstream air filter elements are each microbiocidal air filter elements, wherein said upstream and downstream air filter elements each comprises a demand disinfectant resin, said demand disinfectant resin being in the form of particles of an iodinated strong base anion exchange resin and wherein each of said upstream and downstream air filter elements is spaced apart, by an air space, from said intermediate filter element.

38. A microbiocidal air filter assembly as defined in claim 37 wherein said upstream and downstream air filter elements each comprise an air permeable non-woven fibrous carrier to which said iodinated strong base anion exchange resin is held.

39. A microbiocidal air filter assembly as defined in claim 38 wherein the non-woven carrier of each of said upstream and downstream filter elements has a pair of opposed broad faces spaced apart by a carrier matrix and wherein said air filter component is disposed so as to intersect said air path for air flow communication through each of said broad faces.

40. A microbiocidal air filter assembly as defined in claim 39 wherein particles of said iodinated strong base anion exchange resin are held to each of said broad faces.

41. A microbiocidal air filter assembly as defined in claim 39 wherein particles of said iodinated strong base anion exchange resin are dispersed in the carrier matrix of each of said upstream and downsteam filter elements.

42. A microbiocidal air filter assembly as defined in claim 37 wherein said intermediate air filter element is of planar form.

43. A microbiocidal air filter assembly as defined in claim 37 wherein said intermediate air filter element is of pleated form.

44. A microbiocidal air filter assembly as defined in claim 43 wherein said upstream and downstream air filter elements are each of pleated form.

45. In a system for disinfecting air containing airborne microorganisms, said system comprising
   a) means for providing an air path for the movement of air therethrough, and
   b) an air filter component
      wherein said air filter component is disposed so as to intersect said air path for air flow through said air filter component, the improvement wherein said air filter component consists of an upstream filter element, a downstream filter element and an intermediate air filter element disposed between said upstream and downstream air filter elements, wherein said air filter component is disposed so as to intersect said air path for air flow through each of the air filter elements, wherein said upstream and downstream air filter elements are each microbiocidal air filter elements, wherein said upstream and downstream air filter elements each comprises a demand disinfectant resin, said demand disinfectant resin being in the form of particles of an iodinated strong base anion exchange resin, and wherein each of said upstream and downstream air filter elements is spaced apart, by an air space, from said intermediate filter element.

46. In a system for disinfecting air as defined in claim 45 wherein said upstream and downstream air filter elements each comprise an air permeable non-woven fibrous carrier to which said iodinated strong base anion exchange resin is held.

47. In a system for disinfecting air as defined in claim 46 wherein the non-woven carrier of each of said upstream and downstream filter elements has a pair of opposed broad faces spaced apart by a carrier matrix and wherein said air filter component is disposed so as to intersect said air path for air flow communication through each of said broad faces.

48. In a system for disinfecting air as defined in claim 47 wherein particles of said iodinated strong base anion exchange resin are held to each of said broad faces.

49. In a system for disinfecting air as defined in claim 47 wherein particles of said iodinated strong base anion exchange resin are dispersed in the carrier matrix of each of said upstream and downstream filter elements.

50. In a system for disinfecting air as defined in claim 45 wherein said intermediate air filter element is of planar form.

51. In a system for disinfecting air as defined in claim 45 wherein said intermediate air filter element is of pleated form.

52. In a system for disinfecting air as defined in claim 51 wherein said upstream and downstream air filter elements are each of pleated form.

53. A microbiocidal air filter assembly, for filtering air, having
   a) a housing component defining an air path
   b) an air filter component
   b) an air inlet, and
   d) an air outlet,
      wherein said air filter component consists of a first air filter element and a second air filter element, wherein said air filter component is disposed so as to intersect said air path for air flow communication between said air inlet and said air outlet through each of the air filter elements, wherein said first air filter element is a microbiocidal air filter element and comprises a demand disinfectant resin, said demand disinfectant resin being in the form of particles of an iodinated strong base anion exchange resin and wherein said first air filter element is spaced apart, by an air space, from said second air filter element.

54. A microbiocidal air filter assembly as defined in claim 53 wherein said first air filter element comprises an air permeable non-woven fibrous carrier to which said iodinated strong base anion exchange resin is held.

55. A microbiocidal air filter assembly as defined in claim 54 wherein the non-woven carrier of each of said first filter element has a pair of opposed broad faces spaced apart by a carrier matrix and wherein said air filter component is disposed so as to intersect said air path for air flow communication through each of said broad faces.

56. A microbiocidal air filter assembly as defined in claim 55 wherein particles of said iodinated strong base anion exchange resin are held to each of said broad faces.

57. A microbiocidal air filter assembly as defined in claim 55 wherein particles of said iodinated strong base anion exchange resin are dispersed in the carrier matrix of said first air filter element.

58. A microbiocidal air filter assembly as defined in claim 53 wherein said first air filter element is of planar form.

59. A microbiocidal air filter assembly as defined in claim 53 wherein said first air filter element is of pleated form.

60. A microbiocidal air filter assembly as defined in claim 59 wherein said first and second air filter elements are each of pleated form.

61. In a system for disinfecting air containing airborne microorganisms, said system comprising
   a) means for providing an air path for the movement of air therethough, and
   b) an air filter component
      wherein said air filter component consists of a first air filter element and a second air filter element, wherein said air filter component is disposed so as to intersect said air path for air flow communication between said air inlet and said air outlet through each of the air filter elements, wherein said first air filter element is a microbiocidal air filter element and comprises a demand disinfectant resin, said demand disinfectant resin being in the form of particles of an iodinated strong base anion exchange resin and wherein said first air filter element is spaced apart, by an air space, from said second air filter element.

62. In a system for disinfecting air as defined in claim 61 wherein said first air filter element comprises an air permeable non-woven fibrous carrier to which said iodinated strong base anion exchange resin is held.

63. In a system for disinfecting air as defined in claim 62 wherein the non-woven carrier of said first air filter element has a pair of opposed broad faces spaced apart by a carrier matrix and wherein said air filter component is disposed so as to intersect said air path for air flow communication through each of said broad faces.

64. In a system for disinfecting air as defined in claim 63 wherein particles of said iodinated strong base anion exchange resin are held to each of said broad faces.

65. In a system for disinfecting air as defined in claim 63 wherein particles of said iodinated strong base anion exchange resin are dispersed in the carrier matrix of each of said upstream and downstream filter elements.

66. In a system for disinfecting air as defined in claim 61 wherein said first air filter element is of planar form.

67. In a system for disinfecting air as defined in claim 61 wherein said first air filter element is of pleated form.

68. In a system for disinfecting air as defined in claim 67 wherein said first and second air filter elements are each of pleated form.

69. A microbial air filter assembly as defined in claim 17 wherein said intermediate air filter element is a particulate non-microbiocidal air filter element.

70. In a system for disinfecting air as defined in claim 18 wherein said intermediate air filter element is a particulate non-microbiocidal air filter element.

71. A microbial air filter assembly as defined in claim 37 wherein said intermediate air filter element is a particulate non-microbiocidal air filter element.

72. A microbial air filter assembly as defined in claim 38 wherein said intermediate air filter element is a particulate non-microbiocidal air filter element.

73. A microbial air filter assembly as defined in claim 44 wherein said intermediate air filter element is a particulate non-microbiocidal air filter element.

74. In a system for disinfecting air as defined in claim 45 wherein said intermediate air filter element is a particulate non-microbiocidal air filter element.

75. In a system for disinfecting air as defined in claim 46 wherein said intermediate air filter element is a particulate non-microbiocidal air filter element.

76. In a system for disinfecting air as defined in claim 52 wherein said intermediate air filter element is a particulate non-microbiocidal air filter element.

77. A microbial air filter assembly as defined in claim 19 wherein said air filter component comprises a third air filter element and wherein one of said air filter elements is disposed between the other filter elements so as to define an intermediate filter element.

78. In a system for disinfecting air as defined in claim 20 wherein said air filter component comprises a third air filter element and wherein one of said air filter elements is disposed between the other filter elements so as to define an intermediate filter element.

79. A microbial air filter assembly as defined in claim 53 wherein said air filter component includes a third air filter element and wherein said first air filter element is disposed between the other filter elements so as to define an intermediate filter element.

80. A microbial air filter assembly as defined in claim 57 wherein said air filter component includes a third air filter element and wherein said first air filter element is disposed between the other filter elements so as to define an intermediate filter element.

81. In a system for disinfecting air as defined in claim 61 wherein said air filter component includes a third air filter element and wherein said first air filter element is disposed between the other filter elements so as to define an intermediate filter element.

82. In a system for disinfecting air as defined in claim 67 wherein said air filter component includes a third air filter element and wherein said first air filter element is disposed between the other filter elements so as to define an intermediate filter element.

* * * * *